United States Patent
Swank

(10) Patent No.: US 6,187,824 B1
(45) Date of Patent: Feb. 13, 2001

(54) ZINC OXIDE SOL AND METHOD OF MAKING

(75) Inventor: Thomas F. Swank, Sudbury, MA (US)

(73) Assignee: Nyacol Nano Technologies, Inc., Ashland, MA (US)

(*) Notice: Under 35 U.S.C. 154(b), the term of this patent shall be extended for 0 days.

(21) Appl. No.: 09/382,660

(22) Filed: Aug. 25, 1999

(51) Int. Cl.⁷ .............. B01F 3/12; B01J 13/00; B01J 23/10; A61K 7/42
(52) U.S. Cl. .......... 516/89; 106/286.2; 428/403; 502/304; 424/59
(58) Field of Search ............ 516/89, 93, FOR 112; 424/70.9, 59; 106/425, 426, 419, 286.5, 286.6, 286.2; 252/588; 428/403; 502/304, 340, 342

(56) References Cited

U.S. PATENT DOCUMENTS

| | | | |
|---|---|---|---|
| 5,064,628 | * 11/1991 | Chane-Ching et al. | 502/304 |
| 5,252,356 | * 10/1993 | Yoshida et al. | 427/126.3 |
| 5,376,305 | * 12/1994 | Chane-Ching et al. | 516/89 |
| 5,688,439 | * 11/1997 | Chopin et al. | 516/89 |
| 5,695,747 | * 12/1997 | Forestier et al. | 424/59 |
| 5,827,507 | * 10/1998 | Oshima et al. | 424/59 |
| 6,090,373 | * 7/2000 | Oshima et al. | 424/59 |

* cited by examiner

*Primary Examiner*—Richard D. Lovering
*Assistant Examiner*—Daniel S. Metzmaier
(74) *Attorney, Agent, or Firm*—Alvin Isaacs

(57) ABSTRACT

Disclosed is a zinc-oxide containing sol comprising a core of cerium dioxide sol the surface of which particles is coated with zinc oxide; and the method of making the sol. The sol has a mean particle size of less than 50 nm, is characterized as being clear and transparent and is stabilized to resist agglomeration and particle size increase. An essential part of the disclosed invention is the addition of a positive charged oxide such as yttrium oxide to effect the stabilization before significant changes in transparency, agglomeration and/or particle size increase can occur.

12 Claims, No Drawings

ZINC OXIDE SOL AND METHOD OF MAKING

BACKGROUND OF THE INVENTION

This invention is directed to an improved method for making small particle zinc oxide sols having utility in diverse applications such as cosmetic/UV sunscreens, UV absorption applications in plastics, paint and glass, general catalysis applications, etc.

As is well known and reported in the literature, zinc oxide has the property of being transparent to visible light but opaque to ultra violet (UV) light, thereby making it very useful in UV screening applications where transparency to visible light is desired.

The opacity of a suspension of fine material is dependent upon the particle size of the material, the difference in the refractive index of the dispersed material and the dispersing medium, the degree of absorption of the light by the particles of material and the wavelength of light used in the opacity measurement.

The refractive index (measure of speed of light in the given substance relative to the speed of light in air) of zinc oxide is relatively high, being~2.0, making it a good opacifying pigment, e.g. for paints. Since the refractive index is a fixed characteristic, the approach to alter opacity is to manipulate particle size.

The surface of a zinc oxide crystal effectively reflects visible light. Opacity to visible light reaches a maximum at a particle size of 0.25 micron (250 nm). Smaller particles actually transmit more light than their larger counterparts. This is because particles smaller than~0.25 micron no longer simply reflect back the light, but instead, they scatter it in all directions. Some of this scattered light goes forward, becoming transmitted light.

Zinc oxide owes its opacity below 370 nm to its absorbing power, practically no light being reflected. Because absorption is the mechanism of action, it is possible to make transparent to visible light (non-reflecting) zinc oxide formulations that effectively attenuate UV radiation. Particle sizes on the order of~0.1 micron or less will provide UV absorption while being effectively transparent to visible light. Above this size, "whitening" will occur.

While a search of the patent literature is not necessary in order to demonstrate the efficacy of transparent zinc oxide coatings on a substrate to block transmission of UV radiation, attention is invited to a brief description of the following patents which are thought to be relevant to the instant invention to be described hereinafter.

U.S. Pat. No. 5,252,356 issued to Yoshida et al. discloses a method of producing a transparent zinc oxide film having an even thickness and which is especially useful as a ultraviolet rays cutoff, comprising applying an organic solution of a zinc salt of a 3–7 carbon fatty acid and a chelate compound of a 5–8 carbon diketone to a substrate and then baking. Preferably, the solution further contains an aluminum, indium, tin, or titanium organometallic compound to provide a zinc oxide film having a higher transparency.

U.S. Pat. No. 5,688,439 issued to Chopin et al. discloses colloidal particulates comprising a core of cerium oxide at least partially coated with a sheathing layer of titanium oxide are well suited for the photocatalytic coating of a variety of substrates to impart anti-UV, anti-reflecting and/or anti-staining properties to the substrate. In Col. 1, line 55 through Co. 2, line 18 four alternative methods of effecting precipitation of titanium oxide onto the cerium oxide are disclosed.

The colloidal dispersions comprise colloids in which the particle size thereof ranges from 5–100 nm, preferably 5–30 nm. The colloidal dispersions are said typically to contain a cerium oxide:titanium oxide ratio by weight of 30/70 to 70/30, preferably 50/50.

Advantageously (co. 3, lines 50–55), the colloidal dispersions additionally contain at least one metal serving as a doping agent to reinforce the photocatalytic activity of the titanium dioxide, e.g. palladium, tungsten, platinum or rhodium.

The present invention is also directed to providing a transparent UV absorber consisting of a layer of one oxide over a "core" of another oxide sol. The problem Applicant has confronted in attempting this approach is the difficulty in making very small particle size transparent sols (less than 50 nm) exhibiting optimum screening of UV radiation by prior art methods known to him.

Stated simply, this problem is the task to which to which the present invention is directed.

SUMMARY OF THE INVENTION

In accordance with the present invention this task is solved in an elegant and efficacious manner suitable for commercial manufacture by forming a zinc oxide-containing sol comprising a core of cerium dioxide the surface of which contains a coating of zinc oxide, the zinc oxide/cerium dioxide sol being prepared in the manner described hereinafter in the detailed description of the invention.

DETAILED DESCRIPTION OF THE INVENTION

As was discussed in the BACKGROUND OF THE INVENTION, the present invention is directed to the task of preparing zinc oxide-containing sols having a particle size less than 50 nm (0.05 micrometer).

This task is solved by preparing a sol comprising a cerium dioxide core having on its surface a layer of zinc oxide.

The zinc oxide/cerium dioxide sol is prepared by first mixing zinc oxide powder with an aqueous cerium dioxide sol at a pH of~1.0 to 3.5 and continuing the mixing until the sol is once again "substantially transparent", indicating that the zinc oxide has coated the cerium oxide particles to form a slightly larger particle size sol.

As used herein and in the appended claims, the term "substantially transparent" is used to define an effective transmission of actinic light to be regarded by those skilled in the art as being effectively transparent, although the sol, while clear, has a slight yellow color. In any case, the sol when coated on a transparent support will be regarded as viewed by the eye to be transparent.

The amount of zinc oxide added to the mix to coat the cerium dioxide sol is such that the pH of the coated sol will rise to a range from~2 to~7.

The cerium dioxide sol prior to coating may have a particle size of on the order of about 5 to about 30 nm, preferably from about 5 to about 10 nm.

Following the coating with zinc oxide particles, the resulting zinc oxide/cerium dioxide sol has been found to be stable only for several hours, after which the $ZnO/CeO_2$ composition starts to agglomerate and the particle size increases, changing its appearance from clear (transparent) yellow to an opaque white/yellow dispersion.

Accordingly, a critical part of this invention is the step of stabilization of the sol while it is still substantially transparent.

The desired stability for commercialization of this invention is obtained simply by overcoating the zinc oxide with an effective amount of a positive charged oxide such as yttrium oxide ($Y_2O_3$), samarium oxide ($Sm_2O_3$), aluminum oxide ($Al_2O_3$), zirconium dioxide ($ZrO_2$), etc.

As used herein and in the appended claims, the term "effective amount" of a positive charged oxide connotes an amount sufficient to maintain the stability of the sol, i.e. to maintain its physical properties, e.g. transparency, particle size and freedom from agglomeration such that they were shortly after preparation. The amount of stabilizer to be employed will in part be dependent upon the stabilizer selected and will in part be dependent upon the ratio of ZnO to cerium dioxide in the sol. Accordingly, it is not thought possible positively to recite a range of stabilizer to be used which would at all amounts within that range reflect the stabilization that is desired. For this reason, the amount of stabilizer is recited simply as being an "effective amount". In any case, the selection of a precise amount of stabilizer to use would be within the expected judgment of the skilled worker in the light of this description.

The novel sols of this invention can be applied from an aqueous medium as a coating on the desired substrate in per se known manner, e.g., by immersion, spraying, flowing, vacuum evaporation, etc. In any case the manner of application per se comprises no part of this invention.

EXAMPLE 1

To 40 gms of a 20% $CeO_2$ sol 0.8 gm of ZnO powder is added with mixing. After mixing for 10–20 minutes the sol again appears "transparent", indicating that the ZnO powder has coated the $CeO_2$ to form a slightly larger particle size sol. [It was discovered that with additional time the ZnO/$CeO_2$ composition starts to agglomerate and the particle size increases, changing the appearance of the sol from a clear (transparent) yellow to an opaque white/yellow dispersion, indicating that the ZnO surface is inherently unstable at pH 6, the resultant pH of the composition.] Accordingly, the sol was then stabilized while still clear/yellow by adding 0.21 gms of yttrium oxide powder to the mixing sol. The yttria coats the ZnO with a positive charged oxide, thus stabilizing the sol at this pH. This yields a stable composition consisting of 2.7% dry yttria and 10% dry ZnO based on a dry $CeO_2$ basis.

EXAMPLE 2

Example 1 was repeated, substituting 1.0 gm of ZnO for the 0.8 gm used in Example 1 and then stabilizing once again with 0.21 gm of yttria dioxide. The yield was a stable composition consisting of 2.7% dry yttria and 12.5% dry ZnO based on dry $CeO_2$.

As previously mentioned, the zinc oxide-containing sols of this invention find commercial use in such diverse applications as cosmetic/UV sunscreen use, UV absorption applications in plastics, paint, glass, etc., and general catalysis applications. They may be coated onto the desired substrate in usage in known manner within the expected judgment of the skilled worker and which per se comprises no part of this invention.

Since the present invention is capable of modification without departing from the scope of the invention herein contemplated, it is to be expressly understood that the foregoing description, including the recited examples, is by illustration and not by way of limitation.

What is claimed is:

1. A transparent zinc oxide-containing sol comprising a core of cerium dioxide sol particles the surface of which contains a coating of zinc oxide powder, the zinc oxide-containing sol having a mean particle size less than about 50 nm, the zinc oxide coating being overcoated with a positive charged oxide in an amount effective to stabilize the zinc oxide-containing sol against agglomerating and particle size increase, the amount of zinc oxide being such that the pH of the sol is from about 2 to about 7 prior to applying the positive charged oxide overcoat.

2. A zinc oxide-containing sol as defined in claim 1 wherein the positive charged oxide is yttrium oxide, samarium oxide, aluminum oxide or zirconium dioxide.

3. A zinc oxide-containing sol as defined in claim 1 wherein the positive charged oxide is yttrium oxide.

4. An effectively transparent zinc oxide-containing sol having a mean particle size less than about 50 nm comprising a core of cerium dioxide sol particles the surface of which is coated with zinc oxide, the zinc oxide coating being overcoated with a layer of a positive charged oxide effective to stabilize the zinc oxide-containing sol against loss of effective transparency and against agglomeration and particle size increase.

5. A zinc oxide-containing sol as defined in claim 4 wherein the positive charged oxide is an inorganic oxide selected from the group consisting of yttrium oxide, samarium oxide, aluminum oxide and zirconium dioxide.

6. A zinc oxide-containing sol as defined in claim 4 wherein the zinc oxide is coated on the cerium dioxide sol in an amount such that the pH of the sol is from about 2 to about 7 prior to applying the overcoat of positive charged oxide stabilizer.

7. The method for preparing a stabilized clear and effectively transparent zinc oxide-containing sol having a mean particle size less than less than about 50 nm and being resistant to agglomeration and particle size increase, comprising the steps of:

(1) mixing zinc oxide powder with an aqueous transparent cerium dioxide sol;

(2) continuing the mixing until the sol is once again transparent, indicating the zinc oxide has coated the cerium dioxide particles; and (3) while the sol is still transparent, overcoating the zinc oxide coating with a layer of positive charged oxide in an amount sufficient to stabilize the sol against agglomeration and against particle size increase.

8. A process as defined in claim 7 wherein the positive charged oxide is yttrium oxide, samarium oxide, aluminum oxide or zirconium oxide.

9. A process as defined in claim 7 wherein the positive charged oxide is yttrium oxide.

10. A process as defined in claim 7 wherein the cerium dioxide sol has an initial pH of from about 1.0 to about 3.5 and the amount of zinc oxide added to the aqueous cerium dioxide sol is such that the pH of the coated sol will rise to a range of from about 2.0 to about 7.0.

11. The cerium dioxide sol coated with zinc oxide prepared by the process as defined in claim 7.

12. The cerium dioxide sol coated with zinc oxide prepared by the process as defined in claim 9.

* * * * *